(12) United States Patent
Montchamp et al.

(10) Patent No.: US 6,781,011 B2
(45) Date of Patent: Aug. 24, 2004

(54) BIS-H-PHOSPHINIC ACID DERIVATIVES AS PRECURSORS TO THERAPEUTIC BISPHOSPHONATES AND USES THEREOF

(75) Inventors: Jean-Luc Montchamp, Fort Worth, TX (US); Sylvine Deprele, Fort Worth, TX (US)

(73) Assignee: Texas Christian University, Fort Worth, TX (US)

( * ) Notice: Subject to any disclaimer, the term of this patent is extended or adjusted under 35 U.S.C. 154(b) by 0 days.

(21) Appl. No.: 10/318,731

(22) Filed: Dec. 13, 2002

(65) Prior Publication Data

US 2004/0116673 A1 Jun. 17, 2004

(51) Int. Cl.$^7$ .................................................. C07F 9/28
(52) U.S. Cl. ............................................. 562/13; 562/8
(58) Field of Search ............................... 562/8, 11, 12, 562/13

(56) References Cited

U.S. PATENT DOCUMENTS

| | | | |
|---|---|---|---|
| 3,366,678 A | * 1/1968 | Guttman et al. | ............... 562/14 |
| 5,194,581 A | 3/1993 | Leong | |
| 5,712,261 A | * 1/1998 | Magnin et al. | ............... 514/75 |
| 6,238,687 B1 | 5/2001 | Mao et al. | |
| 6,278,012 B1 | 8/2001 | Hörold et al. | |

OTHER PUBLICATIONS

CA:137:47314 abs of EP 1217004 Jun. 26, 2002.*
CA:108:137664 abs of CN86105761.*
CA:108:16755 abs of Zhurnal Obshchei Khimii by Novikova et al 57(3) pp 525–533 1987.*
CA:111:11554 abs of Dissertation Abstr Int B by C. King 49 (8) pp 3181 1988.*
CA:104:168573 abs of Inorganic Chem byKing et al 25 (8) pp 1290–1292 1986.*
Nifant'ev, Reactions of Acetylenes With Hypophosphorous and Phosphonous Acids, 1986 Plenum Publishing Corporation, article submitted Apr. 23, 1985.
Major, et al, Oral Bisphosphonates, A Review of Clinical Use in Patients with Bone Metastases, Apr. 16, 1999, 2000 American Cancer Society.
Martin et al; Activity of Bisphosphonates against Trypanosoma brucei rhodesiense, J. Med. Chem. 2002, 2904–2914, Jun. 20, 2001.
Szabo et al; An Investigation of Bone Resorption and Dictyostelium discoideum Growth Inhibition by Bisphosphonate Drugs; J. Med. Chem. 2002, 45, 2894–2903; Jun. 20, 2001.
Deprèle et al; Triethylborane–Initiated Room Temperature Radical Addition of Hypophosphites to Olefins: Synthesis of Monosubstituted Phosphinic acids and Esters; Texas Christian University, Jun. 28, 2001.

* cited by examiner

Primary Examiner—Jean F. Vollano
(74) Attorney, Agent, or Firm—Charles D. Gunter, Jr.

(57) ABSTRACT

A novel class of compounds, i.e., 1,1-bis-H-phosphinates (or 1,1-bis-H-phosphinic acid derivatives) are provided. Also provided are novel methods for producing 1,1-bis-H-phosphinates and 1,1-bis-H-phosphinate conjugates. These compounds and conjugates are used are precursors of bisphosphonates and bisphosphonate conjugates, respectively, or as prodrugs directly for treating bone-related and various other diseases.

7 Claims, 6 Drawing Sheets

BIS-H-PHOSPHINIC ACID DERIVATIVES AS PRECURSORS TO THERAPEUTIC BISPHOSPHONATES AND USES THEREOF

BACKGROUND OF THE INVENTION

1. Funding Legend

This invention was produced in part using funds through grant No. P-1435 from the Robert A. Welch Foundation.

2. Field of the Invention

The present invention relates generally to the field of chemistry and drug therapy. More particularly, the present invention provides novel bis-H-phosphinic acid derivatives and methods of producing bis-H-phosphinic acid derivatives. The present invention also provides methods of producing drug or protein conjugates using bis-H-phosphinic acid derivatives and methods of treating bone-related and various other diseases using such derivatives or conjugates.

3. Description of Related Art

Bisphosphonates are used to target molecules to the bone. Pharmaceutical compounds derived from bisphosphonates are used to treat bone cancer, bone infection or deliver steroids to the bone to treat osteoporosis. Bisphosphonates are not only important drugs for the treatment of bone-related diseases, but also important drugs for various other diseases such as high cholesterol. They are currently $1 billion market worldwide. Although they are generally 1-hydroxy-substituted, these compounds have a major limitation. That is, they display poor oral bioavailability because most of the compounds are excreted. Also high dosage causes serious side effects.

Several pharmaceutical companies have been trying to modify bisphosphonates to improve their biological activities. The approach commonly used is to mask the charge of the phosphonate to increase penetration through membranes. However, extensive manipulation is required to modify bisphosphonates which have 3–4 charges at physiological pH.

Bisphosphinates (or phosphinic acid derivatives) are precursors to bisphosphonates. Presently, bisphosphinates oxidize into corresponding bisphosphonates by cumbersome multistep synthesis. Bisphosphinates have been prepared under radial conditions. For example, Nifant'ev (*J. Gen. Chem. USSR* 1986, 56, 680) taught reacting sodium hypophosphite or hypophosphorous acid with alkynes in the presence of peroxides and extensive heat to prepare biophosphinates. Low yields of 1,2-bis-H-phosphinates were sometime obtained from Nifant'ev's method.

Therefore, there is an increasing need for a simple, expeditious and effective method for synthesizing bisphosphonates with increased bioavailability.

SUMMARY OF THE INVENTION

With the foregoing in mind, the present invention provides a novel class of compounds, i.e., 1,1-bis-H-phosphinates (or 1,1-bis-H-phosphinic acid derivatives). Also, the present invention provides a novel method for producing 1,1-bis-H-phosphinates. These compounds are used as precursors of bisphosphonates through chemical or in vivo biological oxidation.

In one embodiment of the present invention, there is provided a 1,1-bis-H-phosphinate compound having a structure of In the structure, R includes Na, H, PhNH3 and alkyl, and R' includes alkyl, COOH, $NH_2$, epoxide, OH, CHO, SH, $CH_2NH_2$, $CH_2$ COO-steroid, $CH_2$-famesyl, $CH_2$-geranyl, N-fluoroquinolones, $CH_2$ S-albumin and $NMe_2CF_2COOH$. Preferably, this compound is a 1,1-bis-H-phosphinate.

In another embodiment of the present invention, there is provided a method for producing a bis-H-phosphinate compound. In this method, a hypophosphorous derivative reacts with an alkyne in the presence of a radical initiator at ambient temperature and pressure conditions. The reaction can be carried out, for example, at room temperature in an open container. Preferably, the radical initiator is an organoborane catalyst, for example, triethylborane.

In still another embodiment of the present invention, there is provided a method for producing a bis-H-phosphinate conjugate. In this method, a hypophosphorous derivative first reacts with an alkyne in the presence of a radical initiator at room temperature in an open container to produce a bis-H-phosphinate compound. The bis-H-phosphinate then reacts with a compound having a pendant functional group to produce a bis-H-phosphinate conjugate. Preferably, the compound having a pendant functional group is a pharmaceutical compound or a protein. An example of the functional group is an alkyne group.

In yet another embodiment of the present invention, there is provided a method for treating an individual having a bone-related disease by administering to the individual an effective dose of a bis-H-phosphinate compound or a bis-H-phosphinate conjugate. Same compound or conjugate can also be used for treating an individual having high cholesterol.

BRIEF DESCRIPTION OF THE DRAWING

Some of the features, advantages, and benefits of the present invention having been stated, others will become apparent as the description proceeds when taken in conjunction with the accompanying drawings in which.

DETAILED DESCRIPTION

The present invention will now be described more fully hereinafter with reference to the accompanying drawings which illustrated preferred embodiments of the invention. This invention may, however, be embodied in many different forms and should not be construed as limited to the illustrated embodiments set forth herein. Rather, these illustrated embodiments are provided so that this disclosure will be thorough and complete, and will fully convey the scope of the invention to those skilled in the art.

A new class of compounds is prepared in one step from alkynes and sodium hypophosphite (or other hypophosphorous derivatives), under the influence of an organoborane catalyst, at room temperature (RT), and in an open flask (air) (reaction (1)).

1, 1-bis-H-phosphinates
1

1, 2-bis-H-phosphinates
2

With R=Na, 1,1-bis-H-phosphinate (compounds 1, the major product) precipitates spontaneously and further can be isolated in pure form by simple filtration. Meanwhile, 1,2-bis-H-phosphinate (compounds 2) is also produced. Other hypophosphorous derivatives (for example, R=H, PhNH$_3$, or alkyl) undergo addition to alkynes under similar conditions, although 1,2-bis-H-phosphinate is usually the major product.

Both 1,1-bis-H-phosphinates (compounds 1) and reaction (1) have not been described previously. 1,1-bis-H-phosphinates are precursors to bisphosphonates (compounds 3) (reaction (2)). This reaction occurs under either chemical or metabolic oxidation.

1, 1-bisphosphonates 3

Figure 1:
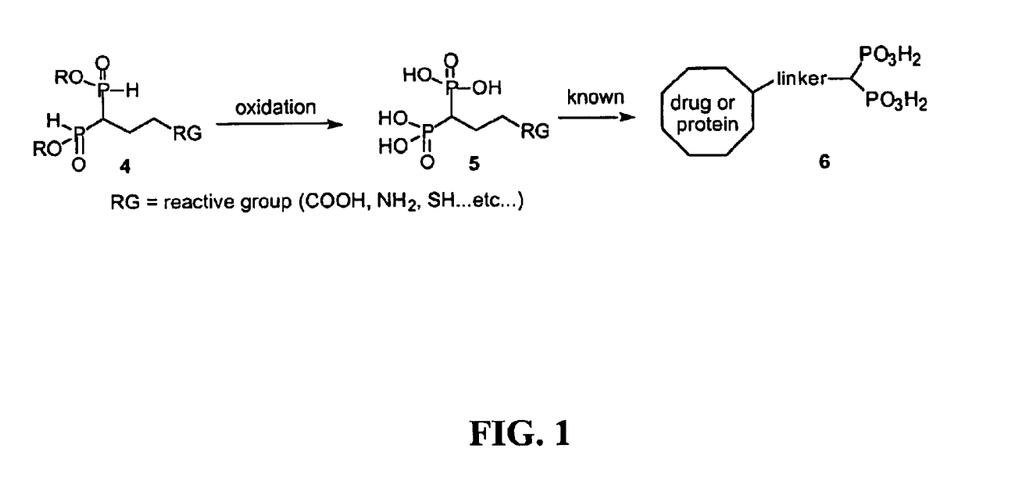
FIG. 1 is a scheme illustrating the process of modifying bisphophonates using bisphosphinates as precursors.

1,1-bis-H-phosphinates with a reaction group (compounds 4) can be converted into 1,1-bisphosphonates (compounds 5), which have been used previously to modify drugs or proteins to construct drug or protein 1,1-bis-H-phosphonate conjugates (compounds 6) (FIG. 1). Examples of the reactive group (RG) include COOH, NH$_2$, and SH.

Figure 2:
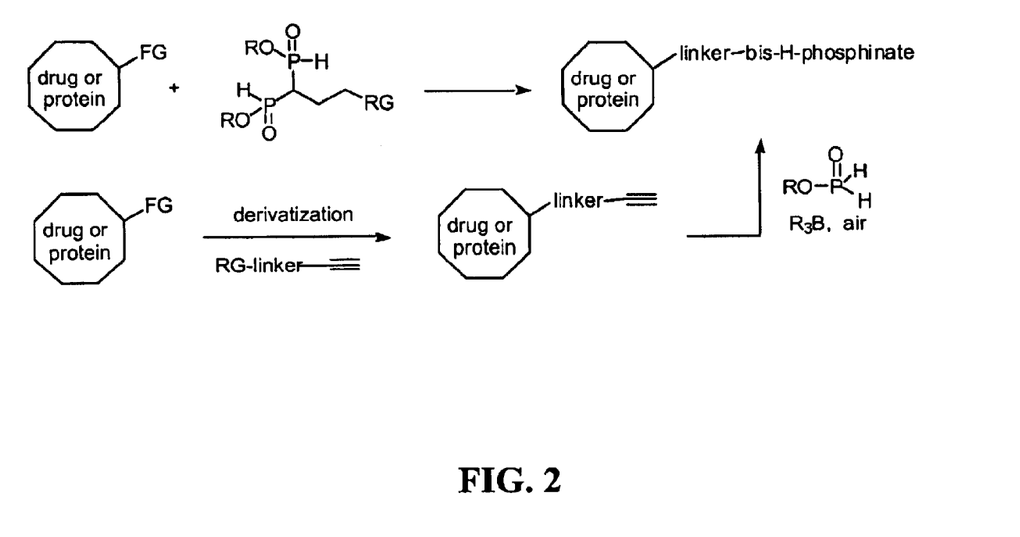
FIG. 2 is a scheme illustrating the process of preparing 1,1-bis-H-phosphinate conjugates.

1,1-bis-H-phosphinate conjugates are prepared from compounds suitably functionalized with a pendant alkyne group (FIG. 2). These conjugates can be easily transformed into bisphosphonates conjugates which are previously difficult to obtain. 1,1-Bis-H-phosphinate conjugates can also be used directly as prodrugs of the corresponding bisphosphonates. Examples of functional group (FG) include OH, NH$_2$, SH, and COOH, while examples of reactive group (RG) include COOH, NH$_2$, epoxide, OH, and CHO.

Figure 3:
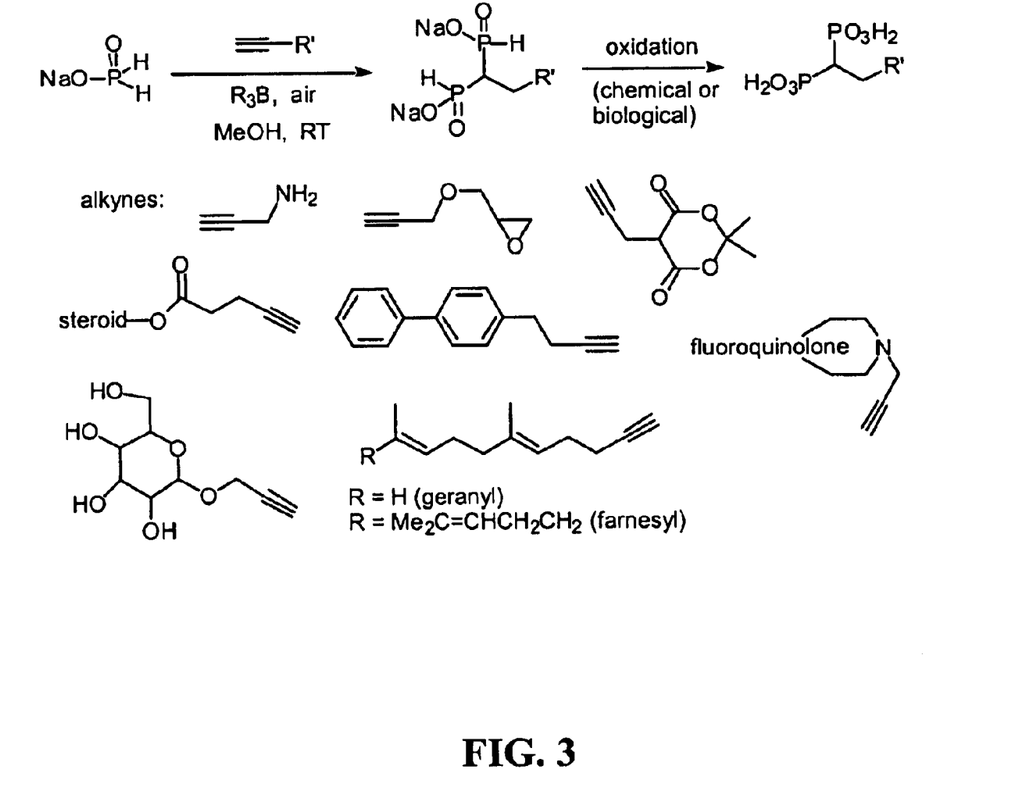
FIG. 3 is a scheme illustrating the process of first preparing disodium 1,1-bis-H-phosphinates and further preparing 1,1-bisphophonates.

Using sodium hypophosphite hydrate (NaH$_2$PO$_2$.H$_2$O) as a substrate, disodium 1,1-bis-H-phosphinate is prepared when an alkyne is added to a solution of sodium hypophosphite hydrate at room temperature in an open flask. 1,1-bis-H-phosphinate is then transformed to 1,1-bis-H-phosphonate under chemical or in vivo biological oxidation (FIG. 3). Examples of alkynes are listed in both FIG. 3 and Table 1.

TABLE 1

Alkynes Used in Formation of Disodium 1,1-Bis-H-phosphinates

| Alkynes | Yield % | $\delta^{31}$P NMR in D$_2$O |
|---|---|---|
| ≡—Oct | 48 | 22.5 |
| ≡—C(OH)(CH$_3$)$_2$ | 39 | 28.7 |
| ≡—CH$_2$NH$_2$ | 48 | 26.5 |
| ≡—CH$_2$TMS | 35 | 27.7 |
| ≡—CH$_2$OH | 37 | 28.1 |

TABLE 1-continued

Alkynes Used in Formation of Disodium 1,1-Bis-H-phosphinates

| Alkynes | Yield % | $\delta^{31}$P NMR in D$_2$O |
|---|---|---|
| (t-butyl propargyl) | 39 | |
| (1-ethynylcyclohexanol) | 44 | 29.2 |
| (propargyl NMe$_2$·CF$_3$COOH) | 50 | 26.1 |
| (propargyl glycidyl ether) | 50 | 26.3 |
| (4-phenyl-1-butyne) | 21 | 26.0 |
|  (estrone propargyl carbonate) | 52 | 24.6 |

Figure 4:
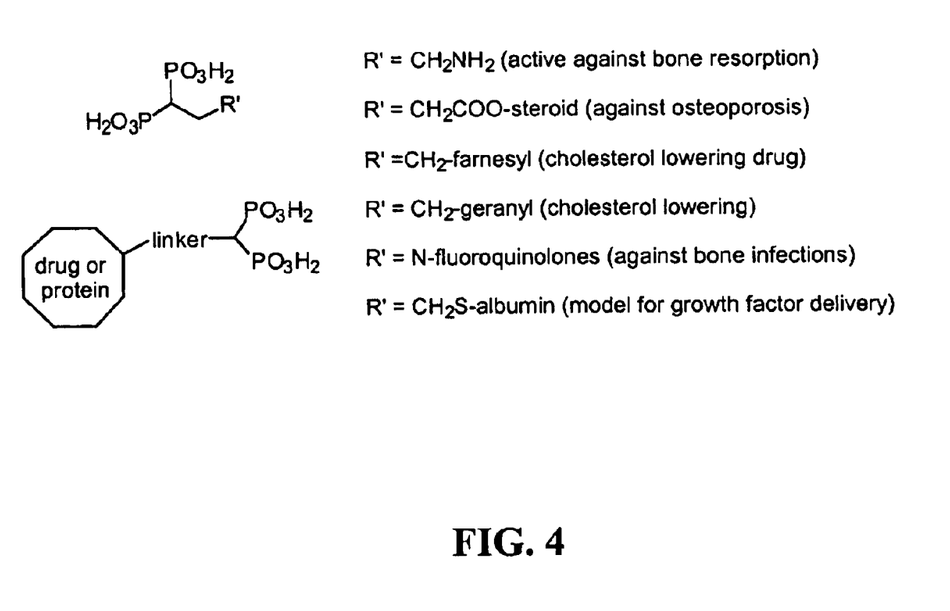
FIG. 4 is a list of bisphosphonates that display important biological activities.

Some bisphosphonates display important biological activities (e.g. against bone disease, osteoporosis, or as cholesterol lowering reagents) (FIG. 4). Currently available syntheses of these bisphosphonates are lengthy and difficult. The task of masking the initial charge of the phosphonates is enormous. In contrast, the present invention provides a simple process to synthesize the bisphosphonates in one or two steps from readily available alkynes. Also, the 1,1-bis-H-phosphinates of the present invention are only diatonic at physiological pH and therefore much more lipophilic. There are suggestions in the literature that H-phosphinic acids undergo biological (metabolic) oxidation to become the actual bisphosphonates (Froestl, et al., *J. Med. Chem.* 1995, 38, 3297). Because they have reduced polarity compared to the corresponding bisphosphonates, 1,1-bis-H-phosphinates should possess increased bioavailability, including oral delivery. Therefore the 1,1-bis-H-phosphinates of the present invention are ideal prodrugs and might be used directly for therapeutic applications.

The present invention provides a 1,1-bis-H-phosphinate compound having a structure of $$\begin{array}{c} \text{RO} \quad \overset{O}{\underset{\parallel}{P}} - H \\ \quad \quad \diagdown \\ \quad \quad \quad R' \\ H \diagup \\ \text{RO} \quad \overset{}{\underset{\parallel}{P}} \\ \quad \quad O \end{array}$$

In the structure, R includes Na, H, PhNH3 and alkyl, and R' includes alkyl, COOH, NH$_2$, epoxide, OH, CHO, SH, CH$_2$NH$_2$, CH$_2$ COO-steroid, CH$_2$-farnesyl, CH$_2$-geranyl, N-fluoroquinolones, CH$_2$ S-albumin and NMe$_2$CF$_2$COOH. Preferably, this compound is a 1,1-bis-H-phosphinate.

The present invention also provides a method for producing a bis-H-phosphinate compound. In this method, a hypophosphorous derivative reacts with an alkyne in the presence of a radical initiator at room temperature in an open container. Further preferably, this method includes filtering the reaction mixture to obtain the bis-H-phosphinate compound in the filtrate. Still preferably, the radical initiator is an organoborane catalyst, for example, triethylborane.

The present invention further provides a method for producing a bis-H-phosphinate conjugate. In this method, a hypophosphorous derivative first reacts with an alkyne in the presence of a radical initiator at room temperature in an open container to produce a bis-H-phosphinate compound. The bis-H-phosphinate then reacts with a compound having a pendant functional group to produce a bis-H-phosphinate conjugate. Preferably, the compound having a pendant functional group is a pharmaceutical compound or a protein. A representative example of the functional group is an alkyne group.

Furthermore, the present invention provides a method for treating an individual having a bone-related disease by administering to the individual an effective dose of a bis-H-phosphinate compound or a bis-H-phosphinate conjugate. Same compound or conjugate can also be used for treating an individual having high cholesterol.

The following examples are given for the purpose of illustrating various embodiments of the invention and are not meant to limit the present invention in any fashion.

EXAMPLE 1

Preparation of Disodium 1,1-Bis-H-phosphinates in Methanol 1,1-bis-H-phosphinate 1,2-bis-H-phosphinate          alkenyl-H-phosphinate An alkyne (2 mmol) was added to a solution of NaH$_2$PO$_2$H$_2$O (5 mmol) in reagent grade methanol (10 mL). Triethylborane (1 M in hexane, 2 mmol) was then added in one portion to the stirred solution at room temperature in open container (i.e., with air). The reaction mixture rapidly became cloudy, and a white precipitate formed. After 2 hours, the mixture was filtered and the solid was washed with cold methanol or ethanol. NMR analysis of the solid at this stage generally showed at least 90% purity. If the solid was sufficiently pure (ca. 98%), it was then dried in vacuum for 24 h over P$_2$O$_5$. The disodium 1,1-bis-H-phosphinates are generally highly hygroscopic and obtained as white amorphous powders.

The filtrate also contained unreacted NaH$_2$PO$_2$, and variable amounts of 1,2-bis-H-phosphinates. For certain substrates, small amounts of monoaddition products (alkenyl-H-phosphinates) may also be observed in the filtrate.

EXAMPLE 2

Preparation of Disodium 1,1-Bis-H-phosphinates in Methanol/Acetone

The reaction was conducted exactly the same as in Example 1, except that methanol (10 mL) was replaced with a solution of methanol (8 mL) and acetone (2 mL). Isolated yields of the disodium 1,1-bis-H-phosphinate were improved without affecting purity.

EXAMPLE 3

Preparation of Disodium 1,1-Bis-H-Phosphinates from Amine-Containing Alkynes

With the exception of propargyl amine, which reacted well with the procedures in Examples 1 & 2, more basic amines such as 1-dimethylamino-2-propyne were poor substrates. However, addition of CF$_3$COOH (1.0–1.2 eq. per basic nitrogen) to the reaction mixture prior to addition of Et$_3$B allowed the reaction to occur in good yield. It is hypothesized that the autocatalytic oxidation of the borane was slowed by complexing to the amine in the absence of acid, and that the efficiency of the radical reaction dropped. The 1,1-bis-H-phosphinate was also obtained as a white or tan precipitate.

EXAMPLE 4

Formation of the 1,2-Bis-H-Phosphinates

Figure 5:
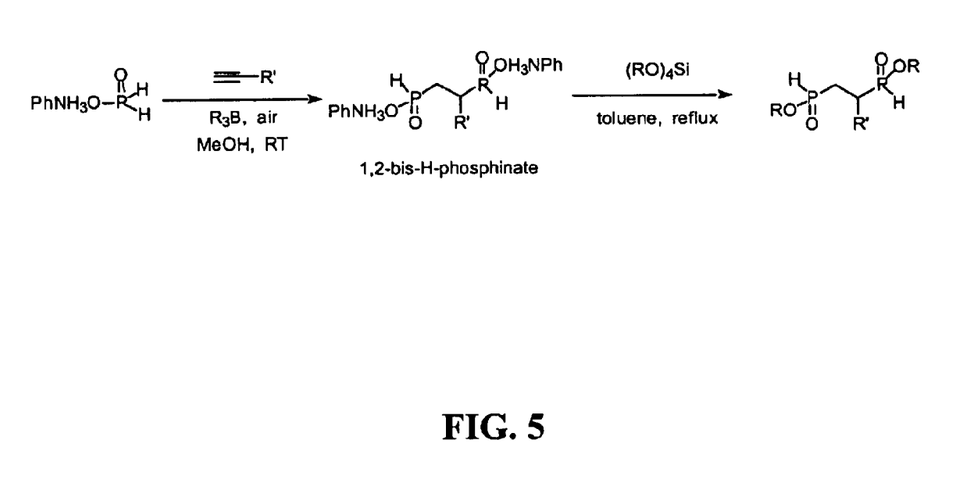
FIG. 5 is a scheme illustrating the process of preparing 1,2-bis-H-phosphinates.

When anilinium hypophosphite (PhNH$_3$O$_2$PH$_2$) was used in place of sodium hypophosphite, no precipitates formed, and the major product was the 1,2-isomer (FIG. 5). With 1-decyne, 1,2-isomer was 50% yield, whereas 1,1-isomer was 15% yield. The product was isolated after esterification of the crude mixture to the bis-alkyl-1,2-bis-H-phosphinate and chromatographic purification.

In detail, an alkyne (2 mmol) was added to a solution of PhNH$_3$O$_2$PH$_2$ (5 mmol) in reagent grade methanol (10 mL). Triethylborane (1 M in hexane, 2 mmol) was then added in one portion to the stirred solution at room temperature in open container. The reaction mixture was stirred for 2 hours, then concentrated under reduced pressure to brown oil. Tetraethyl orthosilicate (5 mmol) and toluene (10 mL) were then added. The mixture was refluxed under N$_2$ for 18–24 h. Concentration in vacuum and chromatographic purification afforded the diethyl-1,2-bis-H-phosphinate.

EXAMPLE 5

Preparation of a Disodium 1,1-Bis-H-phosphinate from Steroid Conjugate

Conjugation of Estrone: Propargyl chloroformate (0.80 mL, 8.2 mmol), was added dropwise to a solution of estrone (2.115 g, 7.8 mmol) and anhydrous pyridine (2.0 mL, 24.7 mmol) in dry CH$_2$Cl$_2$ (20 mL) at room temperature, under N$_2$. The mixture was stirred for 12 h, then EtOAc and aqueous HCl (0.5 N) were added. The organic layer was washed with aqueous NaHCO$_3$ (2×) and brine (1×). Drying over MgSO$_4$ and concentration afforded the estrone conjugate as a slightly impure white solid (2.566 g). This was used without purification in the radical reaction.

Radical Reaction: The steroid conjugate (2.566 g, 7.28 mmol) was dissolved in a mixture of EtOAc (20 mL), acetone (20 mL), and MeOH (30 mL). Since the steroid conjugate was not very soluble in MeOH, EtOAc was added. Sodium hypophosphite (2.304 g, 21.7 mmol) was added and the mixture was almost homogeneous. Et$_3$B (1 M in hexane, 8.0 mL, 8 mmol) was added in one portion, at room temperature and in air. The stirred mixture immediately became cloudy. After 2.5 h, the precipitate was filtered. The white powder contained the 1,1-isomer as the major product, but some 1,2-isomer was also present, as well as a small amount of sodium hypophosphite. The powder was triturated with MeOH (15 mL) for 2 h. Filtration gave the 1,1-isomer product as a white powder (1.990 g, 52%) in good purity after drying in vacuum over P$_2$O$_5$.

Figure 6:
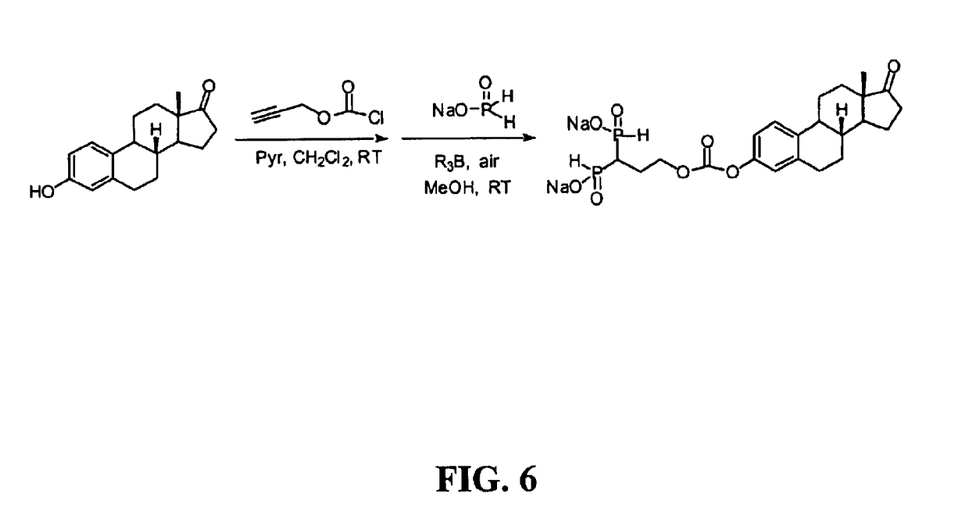
FIG. 6 is a scheme illustrating the process of preparing a disodium 1,1-bis-H-phosphinate from steroid conjugate.

The process of conjugation of estrone and further radical reaction of the steroid conjugate is shown in FIG. 6.

EXAMPLE 6

Preparation of 1,1-Bis-H-phosphinic Acids from the Sodium Salt

The bis-sodium-bis-H-phosphinate salt can be converted to the corresponding acid by acidification with a mineral acid. The most convenient method to avoid separation of inorganic salts involved the use of a polymeric acid such as Amberlite H$^+$. The sodium salt was suspended in methanol, and Amberlite H$^+$ was added. The suspension was stirred vigorously at room temperature, and the resin was filtered. Concentration of the filtrate afforded the corresponding 1,1-bis-H-phosphinic acids as clear, slightly yellow oil, in quantitative yield.

EXAMPLE 7

Esterification of Disodium 1,1-Bis-H-phosphinates

To a suspension of the salt in dry CH$_3$CN was added anhydrous pyridine, EtOH, and pivaloyl chloride, at room temperature and under nitrogen. An exothermic reaction immediately took place. After 4 h, the cloudy mixture was concentrated to a white solid, and partitioned between EtOAc and aqueous HCl (1 N). The organic layer was washed successively with saturated aqueous NaHCO₃ and brine. Drying over MgSO₄ and concentration afforded the ester as colorless oil.

EXAMPLE 8

Oxidation of the 1,1-Bis-H-phosphinates into the Corresponding Bisphosphonates

1,1-bisphosphonates

Because solutions of the disodium 1,1-bis-H-phosphinates were neutral, these compounds were surprisingly resistant to oxidation with bleach or 30% aqueous hydrogen peroxide at room temperature. An aqueous solution of bisphosphinate treated with these oxidants showed no detectable oxidation after 24 h at room temperature. However, gentle heating of the solution at 50–80° C. resulted in quantitative oxidation to the corresponding bisphosphonate. On the other hand, the 1,1-bis-H-phosphinic acids were readily oxidized at room temperature.

In the drawings and specification, there have been disclosed a typical preferred embodiment of the invention, and although specific terms are employed, the terms are used in a descriptive sense only and not for purposes of limitation. The invention has been described in considerable detail with specific reference to these illustrated embodiments. It will be apparent, however, that various modifications and changes can be made within the spirit and scope of the invention as described in the foregoing specification and as defined in the appended claims.

What is claimed is:

1. A 1,1-bis-H-phosphinate compound having a structure wherein R is selected from the group consisting of Na, H, PhNH₃ and alkyl, and R' is selected from the group consisting of alkyl, COOH, NH₂, epoxide, OH, CHO, SH, CH₂NH₂, CH₂COO-steroid, CH₂-farnesyl, CH₂-geranyl, N-fluoroquinolones, CH₂S-albumin and NMe₂CF₃COOH.

2. A method for producing a 1,1-bis-H-phosphinate compound, the method comprising the step of:
reacting a hydrophosphorous precursor with an alkyne in the presence of a radical initiator at room temperature, thereby producing a 1,1-bis-H-phosphinate compound of the formula:

wherein R is selected from the group consisting of Na, H, PhNH₃ and alkyl, and R' is selected from the group consisting of alkyl, COOH, NH₂, epoxide, OH, CHO, SH, CH₂NH₂, CH₂COO-steroid, CH₂-farensyl, CH₂-geranyl, N-fluoroquinolones, CH₂S-albumin and NMe₂CF₃COOH.

3. The method of claim 2, wherein the reaction occurs in an open container.

4. The method of claim 2, wherein the radical initiator is an organoborane catalyst.

5. The method of claim 4, wherein the organoborane catalyst is a trialkylborane.

6. The method of claim 5, wherein the trialkylborane is triethylborane.

7. The method of claim 2, he method further comprising the step of:
filtering reaction mixture upon completion of the reaction to produce a precipitate, wherein the precipitate contains the 1,1-bis-H-phosphinate compound.

* * * * *